US010434171B2

United States Patent
Mauldin et al.

(10) Patent No.: US 10,434,171 B2
(45) Date of Patent: Oct. 8, 2019

(54) **MICROFLUIDIZED *MYCOBACTERIUM AVIUM* FRAGMENTS AS AN ADJUVANT AND CARRIER FOR MUCOSAL VACCINE DELIVERY**

(71) Applicant: United States of America as Represented by Secretary of Agriculture, Washington, DC (US)

(72) Inventors: Richard Mauldin, Loveland, CO (US); Doug Eckery, Fort Collins, CO (US); Lowell Miller, Greeley, CO (US)

( * ) Notice: Subject to any disclaimer, the term of this patent is extended or adjusted under 35 U.S.C. 154(b) by 0 days.

(21) Appl. No.: 15/845,306

(22) Filed: Dec. 18, 2017

(65) Prior Publication Data
US 2018/0177869 A1     Jun. 28, 2018

Related U.S. Application Data

(60) Provisional application No. 62/438,543, filed on Dec. 23, 2016.

(51) Int. Cl.
| | | |
|---|---|---|
| *A61K 39/04* | (2006.01) | |
| *A61K 39/00* | (2006.01) | |
| *A61K 35/74* | (2015.01) | |
| *A61P 15/18* | (2006.01) | |
| *A61P 15/16* | (2006.01) | |
| *A61K 39/39* | (2006.01) | |

(52) U.S. Cl.
CPC .......... *A61K 39/39* (2013.01); *A61K 39/0006* (2013.01); *A61K 39/04* (2013.01); *A61P 15/16* (2018.01); *A61P 15/18* (2018.01); *A61K 35/74* (2013.01); *A61K 2039/54* (2013.01); *A61K 2039/552* (2013.01); *A61K 2039/55594* (2013.01); *A61K 2039/6068* (2013.01)

(58) Field of Classification Search
CPC ...... A61K 2039/55594; A61K 2035/11; A61K 2039/522; A61K 2039/54; A61K 2039/552; A61K 2039/55522; A61K 2039/55561; A61K 2039/58; A61K 2039/6031; A61K 2039/6093; A61K 31/4155; A61K 31/519; A61K 31/60; A61K 35/74; A61K 38/50; A61K 39/00; A61K 39/0006; A61K 39/0011; A61K 39/025; A61K 39/0258; A61K 39/04; A61K 39/39; A61K 47/34; A61K 48/00; A61K 8/85; A61K 9/10; A61K 9/19; C07K 14/35; A61P 15/16; A61P 15/18; A61Q 1/12; C12N 9/0004; C12N 9/0036; C12N 9/0051; C12N 9/0089; C12N 9/18; C12N 9/93; C12R 1/32; C12Y 305/00; Y02A 50/474
See application file for complete search history.

(56) References Cited

U.S. PATENT DOCUMENTS

| | | | |
|---|---|---|---|
| 7,731,939 | B2 | 6/2010 | Miller |
| 9,220,765 | B2 | 12/2015 | Phillips |
| 9,650,423 | B2 | 5/2017 | Van Der Burg |
| 2003/0099668 | A1 | 5/2003 | Bachmann |
| 2007/0192905 | A1 | 8/2007 | Piller |

OTHER PUBLICATIONS

Rutberg, A. T. and Naugle, R. E. (2008) Population effects of immunocontraception in white-tailed deer (*Odocoileus virginianus*) Wildlife Research 35, 494-501.
White P. C. L., and Ward A. I. (2010) Interdisciplinary approaches for the management of existing and emerging human—wildlife conflicts Wildlife Research 37, 623-629.
Gionfriddo J. P., Denicol, A. J., Miller L. A., and Fagerstone K. A. (2011) Efficacy of GnRH immunocontraception of wild white-tailed deer in New Jersey. Wildlife Society Bulletin 35, 142-148.
Miller L. A., Johns B. E. and Killian G. J. (2000) Immunocontraception of white-tailed deer with GnRH vaccine American Journal of Reproductive Immunology 44, 266-274.
Curtis P. D., Pooler R. L, Richmond M. E., Miller L. A., Mattfield G. F., and Quimby F.W. (2002) Comparative effects of GnRH and porcine zona pellucida (PZP) immunocontraceptive vaccines for controlling reproduction in white-tailed deer (*Odocoileus virginianus*) Reproduction 60, 131-141.

*Primary Examiner* — Sarvamangala Devi

(57) ABSTRACT

A vaccine adjuvant and immunogenic composition may be described herein. The vaccine adjuvant may comprise cell wall fragments of the genus *Mycobacterium*, and more particularly, of *M. avium*. The immunogenic composition may include the vaccine adjuvant conjugated to an antigen. For example, cell wall fragments of *M. avium* (herein also referred to as MAF) may be conjugated to an antigen targeting Gonadotropin releasing hormone (GnRH). The MAF-antigen conjugate may be delivered for the purposes of treatment through one of several methods, including intramuscular injection, naso-pharyngeal, or oral.

7 Claims, 2 Drawing Sheets

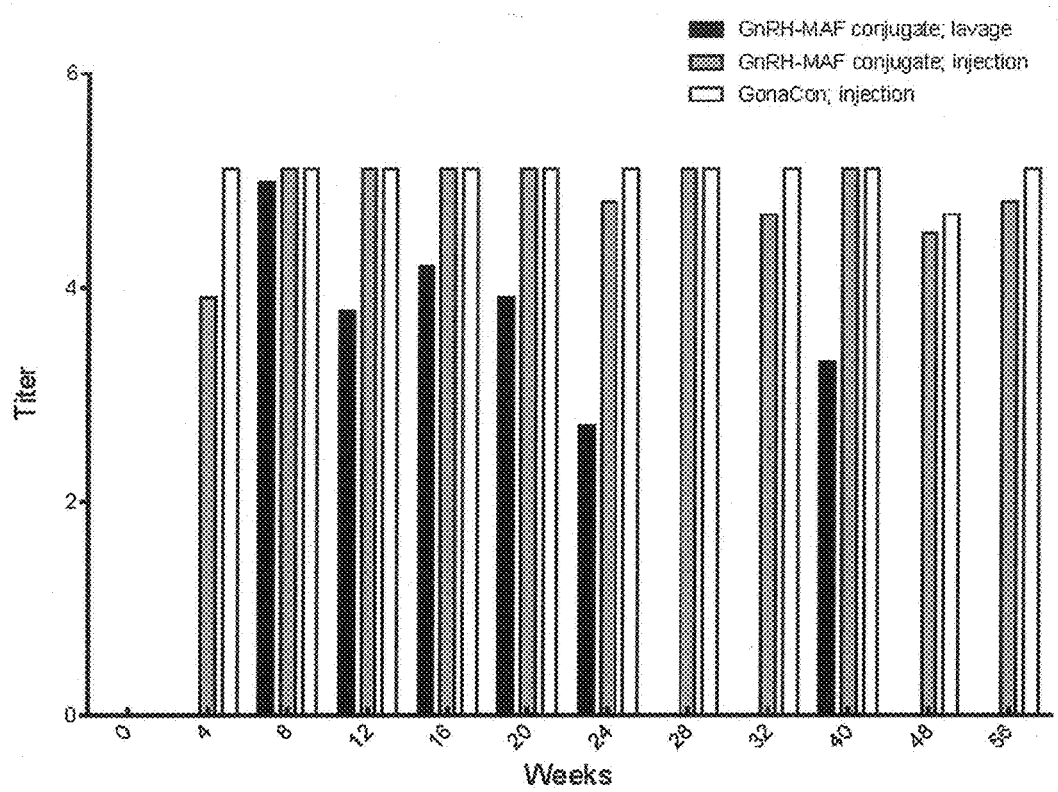
Figure 1. Rat anti-GnRH Median Titers. Titers are expressed as the log of the reciprocal of the titer.

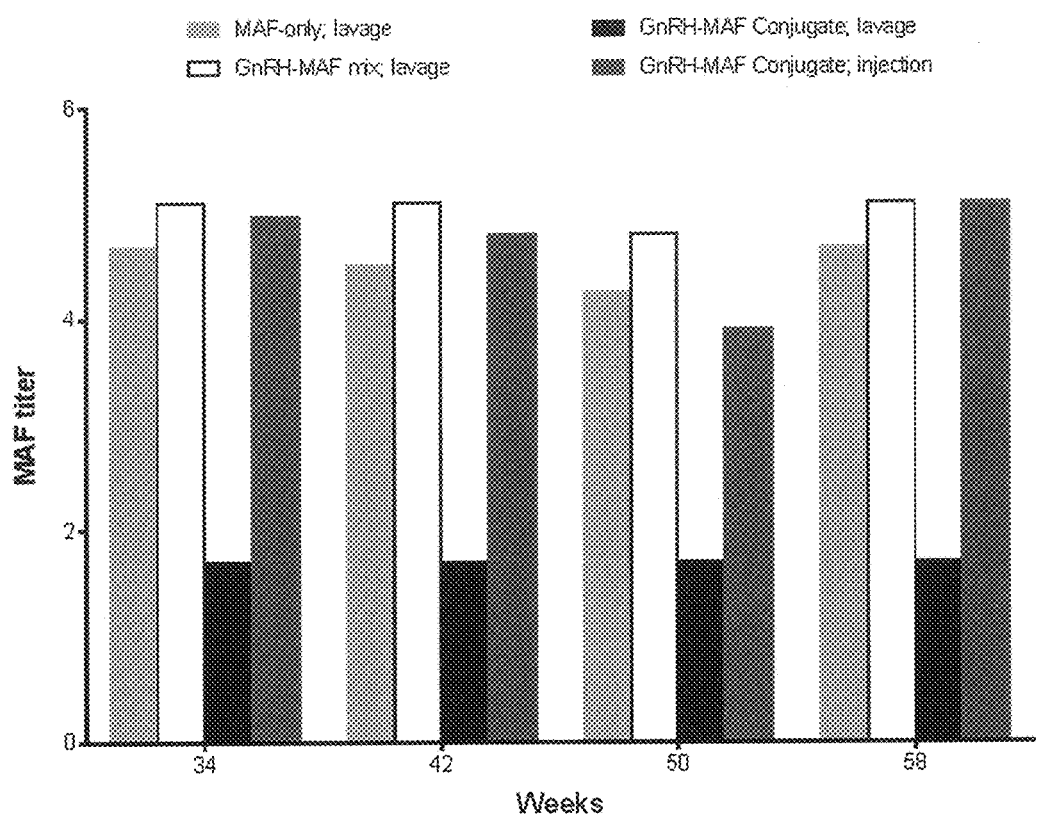
Figure 2. Rat anti-MAF Median Titers. Titers are expressed as the log of the reciprocal of the titer.

MICROFLUIDIZED *MYCOBACTERIUM AVIUM* FRAGMENTS AS AN ADJUVANT AND CARRIER FOR MUCOSAL VACCINE DELIVERY

BACKGROUND

Current trends of human population growth and landscape development show that human-wildlife conflicts are increasing worldwide (e.g. Rutberg, A. T. and Naugle, R. E. (2008) Population effects of immunocontraception in white-tailed deer (*Odocoileus virginianus*) *Wildlife Research* 35, 494-501; White P. C. L., and Ward A. I. (2010) Interdisciplinary approaches for the management of existing and emerging human-wildlife conflicts *Wildlife Research* 37, 623-629; and Gionfriddo J. P., Denicol, A. J., Miller L. A., and Fagerstone K. A. (2011) Efficacy of GnRH immunocontraception of wild white-tailed deer in New Jersey. *Wildlife Society Bulletin* 35, 142-148). As human populations expand and economies grow, the scale of these conflicts increase and new threats emerge, particularly with respect to biodiversity and zoonotic disease. There is thus a need to develop humane, economically viable and environmentally sustainable methods to resolve these conflicts. Only recently fertility control technologies (FCT) have begun to emerge that offer potential for contributing to human-wildlife conflict resolution. In particular, immunocontraception, using a vaccine to generate an immune response to some key component of the target's reproductive system, has moved from theory into practice with the development of "single-shot" injectable vaccines (Miller L. A., Johns B. E. and Killian G. J. (2000) Immunocontraception of white-tailed deer with GnRH vaccine *American Journal of Reproductive Immunology* 44, 266-274; Curtis P. D., Pooler R. L., Richmond M. E., Miller L. A., Mattfeld G. F., and Quimby F. W. (2002) Comparative effects of GnRH and porcine zona pellucida (PZP) immunocontraceptive vaccines for controlling reproduction in white-tailed deer (*Odocoileus virginianus*) *Reproduction* 60, 131-141).

The cell wall of *Mycobacterium* is unique among bacteria, being comprised of a plasma membrane underlying a complex matrix of carbohydrates and lipids, surrounded by an outer "capsule" comprised of polysaccharides and protein. Exact components vary by species, but elements of the mycobacterial cell wall are highly immunogenic in mammals, activating a large array of immune-related cellular receptors on several immune cell types (Britton and Triccas, 2008). Whole, killed bacteria of the genus *Mycobacterium* have long been included in injectable vaccine formulations as an adjuvant. Freunds Complete Adjuvant, comprised of a water/mineral oil emulsion and killed, dried *Mycobacterium* sp. (usually *M. tuberculosis*) has been referred to as the "gold standard for many years" (Colavecchia et al. 2012).

However, development of commercial oral vaccines is challenging as demonstrated by the fact that out of many hundreds of vaccines, only a few orally administered vaccines currently exist e.g. cholera, polio, rabies and BCG. Typically, live particulate forms appear to be most successful in producing an immune response. Oral delivery requires 10-100 fold more antigen in the best of conditions to produce an adequate immune response compared to parenteral delivery. Furthermore, successful oral vaccines have been disease related where there is a potential boost of antibody, resulting in extended protection, in response to disease challenge. This "simulated disease" may have to be a delayed oral boost. A successful oral immunocontraceptive vaccine will need to be economical to produce, it must be protected from the acid and enzymes of the gut and must pass through the mucus layer over the epithelial cells. Against this challenging background research has been carried out into developing orally active immunocontraceptive vaccines. Oral formulations of commercially available injectable immunocontraceptive vaccines have failed to provide contraceptive effects in rabbits and domestic pigs.

Further, whole *Mycobacteria*, even when killed, tend to form clumps which render the cell wall surfaces on the clumps' interior unavailable for chemical manipulation. Thus, there is a need for a product which can improve on the currently-known whole, killed *Mycobacteria* to stimulate an immune response, and further to create a product which can be administered orally.

All of the references cited herein, including U.S. patents and U.S. Patent Application Publications, are incorporated by reference in their entirety.

SUMMARY

A vaccine adjuvant and immunogenic composition may be described herein. The vaccine adjuvant may comprise cell wall fragments of the genus *Mycobacterium*, and more particularly, of *M. avium*. The immunogenic composition may include the vaccine adjuvant conjugated to an antigen. For example, cell wall fragments of *M. avium* (herein also referred to as MAF) may be conjugated to an antigen targeting Gonadotropin releasing hormone (GnRH). The MAF-antigen conjugate may be delivered for the purposes of treatment through one of several methods, including intramuscular injection, naso-pharyngeal, or oral.

BRIEF DESCRIPTION OF THE FIGURES

Advantages of embodiments of the present invention will be apparent from the following detailed description of the exemplary embodiments. The following detailed description should be considered in conjunction with the accompanying figures in which:

Exemplary FIG. 1 shows the results of a study demonstrating that the GnRH-MAF conjugate, in an oral lavage delivery, provides measurable titers at 8-20 weeks, whereas unconjugated GnRH does not provide any measurable titers.

Exemplary FIG. 2 shows the results of a study demonstrating that the combination of GnRH and MAF, through conjugation or mixing, results in measurable MAF titers at 34-58 weeks.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

An "immunogenic composition" is a composition that contains an antigen where administration of the composition to an animal results in an immune response. In addition to the disclosed antigens, other antigens can also be included in the disclosed immunogenic compositions such as those which would be obvious to those of ordinary skill in the art. Such an immune response in the animal may be a humoral and/or a cellular immune response to the antigen. The antigen may also be referred to herein as an "immunogenic agent".

An "immunological response" or "immune response" to an antigen or immunogenic composition is, in an animal, the development, increase, or decrease of a humoral and/or a cellular immune response to the antigen or antigen present in the immunogenic composition. The immune response may be an increased or enhanced immune response (immuno-stimulatory) or a decrease or suppression of an immune response (immuno-suppressant). The immune response may be a systemic and/or localized immune response.

"Vaccination," "vaccinate," "immunization," "immunize," and "inoculate" are synonymous and are the administration of the antigen or immunogenic composition to the animal. Immunization can also include removing immunological cells from the animal, allowing such immunological cells to interact with an antigen in-vitro, and then returning those immunological cells or their progeny back to the animal's body. Exemplary routes of administration of an antigen or immunogenic composition of this invention include, but are not limited to, intramuscular injection, intraperitoneal injection, subdermal injection, intradermal injection, subcutaneous injection, intravenous injection, oral administration, sublingual administration, vaginal administration, rectal administration, transmucosally, transcutaneous adsorption, intranodal administration, intracoronary administration, intraarterial administration, intratracheal administration, intraarticular administration, intraventricular administration, intracranial administration, intraspinal administration, intraocular administration, aural administration, inhalation, and intranasal administration. Vaccination and immunization involves inducing an immune response in the animal receiving the antigen or immunogenic composition.

The appropriate dose of the immunogenic composition of the present invention depends on several variables such as the formulation, the route of administration, the animal's age, the animal's weight, the time of administration, the excretion rate, and reaction irritability. One of ordinary skill in the art can determine the appropriate dose by administering the antigen to the animal and assaying for an increase or, if applicable, a decrease in the immune response.

For immunogenic compositions and antigens, "treatment" refers to any of (i) the prevention of infection or reinfection, as in a traditional vaccine, (ii) the reduction or elimination of symptoms, (iii) the substantial or complete elimination of the pathogen in question, (iv) an enhanced immune response to the antigen or immunogenic composition administered to the animal, and/or (v) the reduction of a hypersensitive immune response in the animal. Treatment may be effected prophylactically (prior to infection or exposure to the antigen or infectious agent) or therapeutically (following infection or exposure to the antigen or infectious agent).

The immunogenic agent or composition may be prepared for administration by formulating an effective immunization dosage of the antigen with a pharmaceutically acceptable carrier or diluent, such as physiological saline or tissue culture medium. The expression "effective immunization dosage" is that amount which will induce immunity in an animal. Immunity is considered as having been induced in an animal when the level of protection for the animal is significantly higher than that of an unvaccinated control group.

The immunogenic composition of this invention may contain one or more pharmaceutically acceptable carriers. Non-limited examples of such carriers include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, stearic acid, magnesium, and mineral oils. In addition to the above ingredients of the pharmaceutical composition according to the present invention may further comprise lubricants, wetting agents, sweetening agents, flavoring agents, emulsifiers, suspending agents, preservatives, etc. Suitable pharmaceutically acceptable carriers and formulations are described in detail in *Remington's Pharmaceutical Sciences* (19th ed., 1995).

Other compounds may be added to the composition provided they do not substantially interfere with the intended activity and efficacy of the composition; whether or not a compound interferes with activity and/or efficacy can be determined, for example, by the procedures utilized below.

The amounts, percentages, and ranges disclosed herein are not meant to be limiting, and increments between the recited amounts, percentages, and ranges are specifically envisioned as part of the invention.

"Optional" or "optionally" means that the subsequently described event or circumstance may or may not occur, and that the description includes instances in which said event or circumstance occurs and instances where it does not. For example, the phrase "optionally comprising X" means that the composition may or may not contain X, and that this description includes compositions that contain and do not contain X.

The term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

According to at least one exemplary embodiment, a vaccine adjuvant may comprise cell wall fragments of the genus *Mycobacterium*.

According to another exemplary embodiment, the cell wall fragments may be from *Mycobacterium avium* cells.

According to another exemplary embodiment, the cell wall fragments may have a mean size of less than 500 nm in diameter.

According to a further exemplary embodiment, an immunogenic composition may comprise a cell wall fragment of the genus *Mycobacterium* conjugated with an antigen.

According to another exemplary embodiment, the cell wall fragment in the immunogenic composition may be from *Mycobacterium avium* cells.

According to another exemplary embodiment, the immunogenic composition may have immunocontraceptive activity.

According to a further exemplary embodiment, a method of vaccination may comprise conducting at least one oral administration of an immunogenic composition comprising a cell wall fragment of *Mycobacterium avium* conjugated with an antigen.

According to another exemplary embodiment, the antigen may target Gonadotropin releasing hormone.

Other exemplary embodiments will be clear to one of ordinary skill in the art without departing from the scope of the claims after reading the following description.

Exemplary Method for Creating Immunogenic Composition

First, whole cells are fragmented to create cell wall fragments. *Mycobacterium* whole cells may be fragmented by any known method. For example, an ultrasound or a microfluidizer may be used. Preferably, the method produces small cell wall fragments (MAF). For example, the mean diameter of cell wall fragments may be about 400 nm.

An exemplary method for fragmentation via microfluidization is further described herein. Approximately 13 g of *M. avium* is added to 110 mL of 0.01 M phosphate buffered saline (PBS, pH 7.2), and further add approximately 2 mL of absolute ethanol (non-denatured). A microfluidizer (M110L, Microfluidics) can be installed with a ceramic interaction chamber (G10Z, 87 μm, Microfluidics), and the microfluidizer system is flushed with approximately 200 mL of 70% isopropanol. The system is then primed with 100 mL of PBS at 6000 psi. To microfluidize the *M. avium*, the *M. avium* suspension is then passed through the microfluidizer at 20,000 psi. The resulting MAF solution can then be spun down with a centrifuge, and the supernatant removed. The spun-down MAF pellets may then be treated with ribonuclease A and deoxyribonuclease in PBS. The treated MAF may then be spun down and washed with PBS, with the supernatant being removed to result in a pellet or paste of MAF cell wall fragments.

Second, the MAF cell wall fragments may be coupled or conjugated with an antigen or immunogen. The conjugation may be performed using any known method. The resulting immunogenic composition may then be used to immunize a target subject.

An exemplary methodology for conjugating MAF to a modified form of GnRH is further described herein. This method utilizes sulfo-succinimidyl-4-(N-maleimidomethyl) cyclohexane-1-carboxylate (S-SMCC) as a cross-linking reagent which links primary amines to sulfhydryl groups. In this method, the MAF provide the amine source. However, native gonadotropin releasing hormone (GnRH), a 10-amino acid peptide, contains no sulfhydryl groups and must be modified to add a sulfhydryl group to allow linkage. This may be done by an adding a glycine "spacer" followed by a cysteine molecule to the C-terminal end of the peptide. The resulting 12-amino acid peptide can then be conjugated to MAF, and is referred to hereinafter as GnRH.

The previously-prepared MAF may be first be suspended in PBS. Then, added to the suspended MAF is S-SMCC in solution. After mixing and centrifuging down the activated MAF and discarding the supernatant, the activated MAF may then be re-suspended in PBS adjusted to pH of 6.0. After spinning down once more, the activated MAF is then re-suspended in PBS (pH 7.2), and GnRH (in PBS solution) is added to it. After mixing for about 30 min, the resulting conjugate may be dialyzed to remove unconjugated GnRH or used as is for animal treatment/immunization.

The immunization may include a single administration or multiple administrations over time. Further, the administrations may be intramuscular injection, naso-pharyngeal, or oral.

Testing and Characterization

In testing the effectiveness of the immunogenic composition via various administration routes and protocols, studies were conducted to both measure the resulting concentration of antibodies in a laboratory animal study and to measure the practical effect of the immunogenic composition on the animal subjects. For example, in the examples described below, the immunogenic agent may be an immunocontraceptive agent targeting GnRH, and thus a vaccinated animal may display reduced or eliminated reproductivity.

In the present examples, the immunogenic composition was created using the above method. A GnRH-specific antigen was used and conjugated to the MAF using a two-step 1-Ethyl-3-(3-dimethylaminopropyl)carbodiimide coupling (Hermanson, G. T. (2013) *Bioconjugate Techniques, 3rd Edition*, Elsevier Inc). The antigen used was a GnRH French recombinant construct hereinafter termed "FrReco." FrReco consists of seven GnRH monomers combined through 2 cystine linkages to form a heptamer of 50,000 MW.

For the animal studies, laboratory rats were used as a model mammalian species. Nulliparous maturing outbred Wistar strain female rats were sourced from a registered breeder and typically weighed between 180 and 200 g on arrival. The rats were housed in wire mesh cages, 2-3 animals per cage, in temperature and humidity-controlled rooms on a 12 hr light:12 hr dark cycle and provided with ad libitum water and standard laboratory rat diet (IPS 5002 pellets). Animals were given two weeks of acclimatization before being randomly assigned to experimental groups.

During each trial blood (maximum volume 0.5 ml) was collected from each rat prior to treatment to obtain baseline values and 45 days later, i.e. 15 days after all dosing had been completed (see below). For blood sampling, all animals were anaesthetized using sevofluorane. Anti-GnRH antibody titres in spun blood serum samples were then evaluated using an indirect ELISA technique based on that used by Miller et al., Levy et al. (Levy, J. K., Miller, L. A., Crawford, P., Ritchey, J. W., Ross, M. K. & Fagerstone, K. A. (2004) GnRH immunocontraception of male cats. *Theriogenology*, 62, 1116-1130) and Bender et al. (Bender S. C., Bergman D. L., Wennin K. M., Miller L. A., Slate D., Jackson F. R. and Rupprecht C. E. (2009). No adverse effects of simultaneous vaccination with the immunocontraceptive GonaCon™ and a commercial rabies vaccine on rabies virus neutralizing antibody production in dogs. *Vaccine* 27, 7210-7213) and specifically adapted for the laboratory rat. As presented herein, titres are the highest 1:X,000 dilution at which an antibody is detected. For clarity, the words "titre" and "titer" are interchangeable.

For reproductive studies, three weeks after completion of dosing, adult Wistar strain males were introduced into the females' cages. After a further 10 days females were housed singly. Subsequently produced pups were removed and counted.

EXAMPLES

Example 1

MAF-FrReco conjugates were prepared using both ultrasound (MAF-U) and microfluidization (MAF-M) to create the cell wall fragments. Groups were set up for intramuscular (IM) injection, naso-pharyngeal lavage, and oral lavage. In each group, the conjugate was in phosphate-buffered saline (PBS). After initial administrations, boosters were given at 15 day intervals. A positive control of Gona-Con (a known commercial injected vaccine) was administered to one group. Further, negative controls of MAF-M without an antigen conjugated thereto were also conducted for each administration route. Table 1a summarizes the experimental setup:

TABLE 1a

Experimental design for Example 1

| Group | Formulation | Route | Dose (FrReco) | No. of doses |
|---|---|---|---|---|
| 1 | MAF-U-FrReco | IM injection | 0.2 mL (200 µg) | 3 |
| 2 | MAF-U-FrReco | Naso-pharyngeal | 0.05 mL (50 µg) | 3 |
| 3 | MAF-U-FrReco | Oral | 0.5 mL (500 µg) | 3 |
| 4 | MAF-M-FrReco | IM injection | 0.2 mL (200 µg) | 3 |
| 5 | MAF-M-FrReco | Naso-pharyngeal | 0.05 mL (50 µg) | 3 |
| 6 | MAF-M-FrReco | Oral | 0.5 mL (500 µg) | 3 |
| 7 | MAF-M (negative control) | IM injection | 0.2 mL (0 µg) | 3 |
| 8 | MAF-M (negative control) | Naso-pharyngeal | 0.05 mL (0 µg) | 3 |
| 9 | MAF-M (negative control) | Oral | 0.05 mL (0 µg) | 3 |
| 10 | GonaCon (positive control) | IM injection | 0.2 mL | 1 |

In each group, blood samples were collected, as previously mentioned, 45 days after administering the initial dose. Further, additional blood samples were collected at 26 weeks after administering the initial dose. Table 1b summarizes the data from the blood samples taken 45 days after initial administration, and Table 1c summarizes the data from the blood samples taken 26 weeks after initial administration. Groups without any difference between them were pooled for the purposes of summarizing the data:

TABLE 1b

Titres for groups in Example 1 in samples taken 45 days after initial administration

| Treatment | N | Titre (1: X,000) | | | | | | | | | | | % with titre |
|---|---|---|---|---|---|---|---|---|---|---|---|---|---|
| | | 0 | 2 | 4 | 8 | 16 | 32 | 64 | 128 | 256 | 512 | 1024 | 2048 | |
| Oral MAF-FrReco (Groups 3&6) | 20 | 7 | 2 | 2 | 5 | 2 | 1 | 1 | — | — | — | — | — | 65% |
| Naso-pharyngeal MAF-FrReco (Groups 2&5) | 19 | 9 | 1 | — | 3 | 2 | 1 | 1 | 2 | — | — | — | — | 53% |
| IM MAF-FrReco (Groups 1&4) | 19 | 1 | — | 1 | — | — | 2 | 6 | 3 | 3 | 2 | 1 | — | 95% |
| GonaCon (Group 10) | 10 | — | — | — | — | — | — | — | — | — | 2 | 2 | 6 | 100% |
| Negative Controls (Groups 7, 8, & 9) | 15 | 15 | — | — | — | — | — | — | — | — | — | — | — | 0% |

TABLE 1c

Titres for groups in Example 1 in samples taken 26 weeks after initial administration

| Treatment | N | Titre (1: X,000) | | | | | | | | | | | % with titre |
|---|---|---|---|---|---|---|---|---|---|---|---|---|---|
| | | 0 | 2 | 4 | 8 | 16 | 32 | 64 | 128 | 256 | 512 | 1024 | 2048 | |
| Oral MAF-FrReco (Groups 3&6) | 20 | 11 | 1 | — | — | 2 | 5 | 1 | — | — | — | — | — | 45% |
| Naso-pharyngeal MAF-FrReco (Groups 2&5) | 19 | 11 | — | 1 | 2 | 1 | 2 | 2 | — | — | — | — | — | 42% |

TABLE 1c-continued

Titres for groups in Example 1 in samples taken 26 weeks after initial administration

| Treatment | N | 0 | 2 | 4 | 8 | 16 | 32 | 64 | 128 | 256 | 512 | 1024 | 2048 | % with titre |
|---|---|---|---|---|---|---|---|---|---|---|---|---|---|---|
| IM MAF-FrReco (Groups 1&4) | 19 | 9 | — | 1 | — | 2 | 3 | 3 | 1 | — | — | — | — | 53% |
| GonaCon (Group 10) | 10 | — | — | — | — | — | — | — | 4 | 4 | 2 | — | — | 100% |

As is clear, the MAF-FrReco conjugate as an immunogenic composition is effective in all tested administrations. Further, the conjugate is able to penetrate the mucosal membranes and cause an antibody response in both of the naso-pharyngeal and oral applications, a surprising and unexpected result.

Example 2

MAF-FrReco conjugates were prepared using microfluidization (MAF-M) to create the cell wall fragments. To test the effect on reproductivity by oral administration, groups were set up for intramuscular (IM) injection and oral lavage. After initial administrations, boosters were given at equal intervals over a period of 30 days. A negative control of untreated rats was used. Table 2a summarizes the experimental setup:

TABLE 2a

Experimental design for Example 2

| Group | Formulation | Route | Dose (FrReco) | No. of doses |
|---|---|---|---|---|
| 1 | MAF-FrReco | Oral lavage | 0.5 mL (2500 µg) | 6 |
| 2 | MAF-FrReco | IM injection | 200 µg | 3 |
| 3 | Contol (untreated) | N/A | — | — |

In each group, blood samples were collected, as previously mentioned, 45 days after administering the initial dose. Further, additional blood samples were collected at 20 weeks after administering the initial dose. Table 2b summarizes the data from the blood samples taken 45 days after initial administration, and Table 2c summarizes the data from the blood samples taken 20 weeks after initial administration:

TABLE 2b

Titres for groups in Example 2 in samples taken 45 days after initial administration

| Treatment | N | 0 | 2 | 4 | 8 | 16 | 32 | 64 | 128 | 256 | 512 | 1024 | 2048 | % with titre |
|---|---|---|---|---|---|---|---|---|---|---|---|---|---|---|
| Oral MAF-FrReco | 10 | 4 | — | — | — | — | — | 1 | — | 1 | 4 | — | — | 60% |
| IM MAF-FrReco | 10 | — | — | — | — | — | — | — | — | — | — | 1 | 9 | 100% |
| Control | 9 | 9 | — | — | — | — | — | — | — | — | — | — | — | 0% |

TABLE 2c

Titres for groups in Example 2 in samples taken 20 weeks after initial administration

| Treatment | N | 0 | 2 | 4 | 8 | 16 | 32 | 64 | 128 | 256 | 512 | 1024 | 2048 | % with titre |
|---|---|---|---|---|---|---|---|---|---|---|---|---|---|---|
| Oral MAF-FrReco | 10 | 7 | — | — | — | 1 | 2 | — | — | — | — | — | — | 30% |
| IM MAF-FrReco | 10 | — | — | — | — | — | 1 | 5 | 2 | 2 | — | — | — | 100% |

Concurrently with the collection of the blood samples summarized above, reproductive studies were carried out as described above. The number of rats which bred and the mean litter sizes are summarized in Tables 2d and 2e:

TABLE 2d

Numbers of breeding rats in Example 2

| Treatment | N | n Bred | % Bred |
|---|---|---|---|
| Oral MAF-FrReco | 10 | 4 | 40% |
| IM MAF-FrReco | 10 | 0 | 0% |
| Control | 9 | 7 | 78% |

TABLE 2e

Mean litter size and standard deviation for all rats in Example 2.

| Treatment | N | Mean | SD |
|---|---|---|---|
| Oral MAF-FrReco | 9* | 3.11 | 4.91 |
| IM MAF-FrReco | 10 | 0.00 | 0.00 |
| Control | 9 | 7.22 | 5.17 |

*Litter size unknown for one rat

The above results demonstrate that (1) the MAF-FrReco conjugate has immunocontraceptive activity, as shown by the injected studies, and (2) that oral lavage is an effective treatment mechanism using the disclosed conjugate.

Example 3

In another study, young female Wistar rats were lavaged naso-orally bi-weekly, three times with MAF-GnRH conjugate, along with (1) an injected, positive control (GonaCon), (2) the MAF-GnRH conjugate-injected (to determine if the invention is immunogenic when given parenterally) and (3) other naso-orally lavaged controls (i.e. GnRH-only and MAF-GnRH unconjugated). FIG. 1 shows the development of anti-GnRH serum titers through time, demonstrating that both GonaCon and the MAF-GnRH conjugate-injected yielded a strong immunogenic response. The bars represent the antibody response in rats lavaged with the MAF-GnRH conjugate and indicate a positive effect of treatment while the other control treatments yielded no little or no response. Relatedly, FIG. 2 demonstrates that the applications result in measurable MAF titers at 34-58 weeks.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A vaccine adjuvant comprising cell wall fragments of *Mycobacterium avium* cells, wherein the cell wall fragments are created by microfluidization to have a diameter size of less than 500 nm.

2. An immunogenic composition comprising the vaccine adjuvant of claim 1 and an antigen, wherein the adjuvant and the antigen are conjugated to together.

3. The immunogenic composition of claim 2, wherein the antigen is the native Gonadotropin releasing hormone (GnRH) peptide antigen.

4. The immunogenic composition of claim 3, wherein the composition has immunocontraceptive activity.

5. The immunogenic composition of claim 2, wherein the adjuvant and the antigen are conjugated to each other via a spacer.

6. A method of immunization of an animal comprising administration of an effective immunization dosage of the immunogenic composition of claim 2.

7. A method of immunization of an animal comprising oral administration of an effective immunization dosage of the immunogenic composition of claim 3.

* * * * *